(12) United States Patent
Tsals et al.

(10) Patent No.: US 9,327,086 B2
(45) Date of Patent: May 3, 2016

(54) NEEDLE SHIELD AND ADAPTER FIXEDLY ATTACHED TO SYRINGE

(75) Inventors: Izrail Tsals, Newtown, PA (US); Christopher Evans, Long Valley, NJ (US); Brian Costello, Union, NJ (US)

(73) Assignee: SID Technologies, LLC, Newtown, PA (US)

( * ) Notice: Subject to any disclaimer, the term of this patent is extended or adjusted under 35 U.S.C. 154(b) by 0 days.

(21) Appl. No.: 13/583,096

(22) PCT Filed: Mar. 11, 2011

(86) PCT No.: PCT/US2011/028072
§ 371 (c)(1),
(2), (4) Date: Sep. 6, 2012

(87) PCT Pub. No.: WO2011/112916
PCT Pub. Date: Sep. 15, 2011

(65) Prior Publication Data
US 2013/0006189 A1 Jan. 3, 2013

Related U.S. Application Data

(60) Provisional application No. 61/339,933, filed on Mar. 12, 2010.

(51) Int. Cl.
*A61M 5/46* (2006.01)
*A61M 5/42* (2006.01)
(Continued)

(52) U.S. Cl.
CPC .............. *A61M 5/425* (2013.01); *A61M 5/158* (2013.01); *A61M 5/24* (2013.01); *A61M 5/3287* (2013.01); *A61M 5/46* (2013.01); *A61M 2005/1585* (2013.01)

(58) Field of Classification Search
CPC ........ A61M 5/21; A61M 5/2033; A61M 5/24; A61M 5/326; A61M 5/3287; A61M 5/425
USPC .................. 604/192, 186–187, 115, 198.506, 604/410–414
See application file for complete search history.

(56) References Cited

U.S. PATENT DOCUMENTS

| 2,198,666 A | 4/1940 | Gruskin |
| 2,701,566 A * | 2/1955 | Krug ...................... A61M 5/20 |
| | | 604/154 |

(Continued)

FOREIGN PATENT DOCUMENTS

| EP | 0216460 B1 | 9/1990 |
| EP | 0457477 A1 | 11/1991 |

(Continued)

OTHER PUBLICATIONS

Int'l Preliminary Report on Patentability issued Sep. 27, 2012 in Int'l Application No. PCT/US2011/028072.

(Continued)

*Primary Examiner* — Bhisma Mehta
*Assistant Examiner* — Matthew A Engel
(74) *Attorney, Agent, or Firm* — Panitch Schwarze Belisario & Nadel LLP

(57) ABSTRACT

An assembly for use with a syringe having a barrel and a needle includes a sealing element surrounding and positioned over at least a portion of the distal end of the syringe. An adapter at least partially surrounds the sealing element and is positioned over the distal end of the syringe. The adapter has a first skin contacting surface positioned at a distal end thereof. At least a portion of the first skin contacting surface extends generally parallel to at least a terminal end of the needle. The adapter also has a second skin contacting surface positioned proximally relative to the terminal end of the needle and at an angle to the first skin contacting surface. A needle shield at least partially surrounds and is removably positioned over at least one of the adapter, the sealing element and the syringe barrel.

5 Claims, 10 Drawing Sheets

(51) Int. Cl.
*A61M 5/24* (2006.01)
*A61M 5/158* (2006.01)
*A61M 5/32* (2006.01)

(56) References Cited

U.S. PATENT DOCUMENTS

| | | | | |
|---|---|---|---|---|
| 3,324,854 | A * | 6/1967 | Weese | A61M 5/425 604/115 |
| 3,459,177 | A | 8/1969 | Deuschle | |
| 3,472,227 | A * | 10/1969 | Burke | A61M 5/343 604/243 |
| 3,523,531 | A * | 8/1970 | Burke | A61M 5/343 604/264 |
| 3,523,532 | A * | 8/1970 | Burke | A61M 5/343 604/240 |
| 3,556,099 | A * | 1/1971 | Knight | A61M 5/24 604/232 |
| 3,756,235 | A * | 9/1973 | Burke | A61M 5/343 604/240 |
| 3,903,887 | A * | 9/1975 | Antoshkiw | A61M 5/32 604/272 |
| 4,240,433 | A * | 12/1980 | Bordow | A61B 17/3496 604/162 |
| 4,332,248 | A | 6/1982 | DeVitis | |
| 4,393,870 | A | 7/1983 | Wagner | |
| 4,568,346 | A * | 2/1986 | van Dijk | A61J 1/2096 604/234 |
| 4,631,057 | A | 12/1986 | Mitchell | |
| 4,737,144 | A | 4/1988 | Choksi | |
| 4,747,837 | A | 5/1988 | Hauck | |
| 4,795,445 | A * | 1/1989 | Jensen | A61M 5/34 604/240 |
| 4,801,295 | A | 1/1989 | Spencer | |
| 4,850,996 | A | 7/1989 | Cree | |
| 4,958,625 | A * | 9/1990 | Bates | A61B 10/0275 600/562 |
| 4,966,589 | A * | 10/1990 | Kaufman | A61M 25/02 128/DIG. 26 |
| 4,998,920 | A | 3/1991 | Johnson | |
| 5,053,018 | A | 10/1991 | Talonn et al. | |
| 5,084,030 | A | 1/1992 | Byrne et al. | |
| 5,108,378 | A * | 4/1992 | Firth | A61M 5/3243 604/192 |
| 5,171,214 | A * | 12/1992 | Kolber | A61J 1/2096 206/222 |
| 5,197,953 | A * | 3/1993 | Colonna | A61M 5/3243 604/110 |
| 5,250,037 | A * | 10/1993 | Bitdinger | A61M 5/3202 604/192 |
| 5,282,793 | A | 2/1994 | Larson | |
| 5,364,362 | A * | 11/1994 | Schulz | A61D 1/025 604/115 |
| 5,393,497 | A * | 2/1995 | Haber | A61J 1/2089 137/68.11 |
| 5,437,640 | A | 8/1995 | Schwab | |
| 5,496,288 | A | 3/1996 | Sweeney | |
| 5,520,653 | A | 5/1996 | Reilly et al. | |
| 5,527,287 | A | 6/1996 | Miskinyar | |
| 5,669,888 | A | 9/1997 | Trapp | |
| 5,855,839 | A | 1/1999 | Brunel | |
| 5,893,845 | A | 4/1999 | Newby et al. | |
| 5,976,102 | A * | 11/1999 | Epstein | A61B 17/00491 222/145.5 |
| 5,984,890 | A * | 11/1999 | Gast | A61M 37/0069 604/57 |
| 6,117,108 | A | 9/2000 | Woehr et al. | |
| 6,200,291 | B1 | 3/2001 | Di Pietro | |
| 6,494,865 | B1 | 12/2002 | Alchas | |
| 6,503,229 | B2 * | 1/2003 | King | A61B 5/1405 604/110 |
| 6,569,123 | B2 * | 5/2003 | Alchas | A61M 5/46 604/192 |
| 6,607,509 | B2 * | 8/2003 | Bobroff | A61M 5/158 604/136 |
| 6,666,844 | B1 * | 12/2003 | Igo | A61B 17/00234 604/115 |
| 6,689,118 | B2 | 2/2004 | Alchas et al. | |
| 6,776,776 | B2 * | 8/2004 | Alchas | A61M 5/3129 604/117 |
| 6,921,384 | B2 | 7/2005 | Reilly et al. | |
| 6,939,322 | B2 * | 9/2005 | Crank | A61M 25/0068 604/117 |
| 7,052,483 | B2 * | 5/2006 | Wojcik | 604/162 |
| 7,438,703 | B2 * | 10/2008 | Barrus | A61B 5/14 128/919 |
| 7,794,445 | B2 * | 9/2010 | Dalton | A61M 5/158 604/263 |
| 7,938,808 | B2 | 5/2011 | Pessin | |
| 8,083,715 | B2 | 12/2011 | Sonoda et al. | |
| 8,556,861 | B2 * | 10/2013 | Tsals | 604/187 |
| 8,876,764 | B2 * | 11/2014 | Tsals | A61B 5/150748 604/115 |
| 2001/0056265 | A1 * | 12/2001 | Heinz | A61M 5/3135 604/227 |
| 2002/0077599 | A1 * | 6/2002 | Wojcik | A61M 5/158 604/162 |
| 2002/0193744 | A1 | 12/2002 | Alesi et al. | |
| 2003/0050602 | A1 | 3/2003 | Pettis et al. | |
| 2003/0093032 | A1 | 5/2003 | Py et al. | |
| 2003/0199822 | A1 | 10/2003 | Alchas et al. | |
| 2004/0010234 | A1 | 1/2004 | Hung et al. | |
| 2004/0147901 | A1 * | 7/2004 | Py | A61M 5/2033 604/506 |
| 2006/0079920 | A1 | 4/2006 | Schraga | |
| 2007/0118077 | A1 | 5/2007 | Clarke et al. | |
| 2007/0250016 | A1 | 10/2007 | Pech et al. | |
| 2008/0154205 | A1 | 6/2008 | Wojcik | |
| 2009/0082732 | A1 * | 3/2009 | Hillman | A61B 5/158 604/164.08 |
| 2010/0137831 | A1 * | 6/2010 | Tsals | A61M 5/3243 604/506 |
| 2011/0077602 | A1 | 3/2011 | Yokota et al. | |
| 2011/0224609 | A1 * | 9/2011 | Tsals | A61M 5/3216 604/117 |

FOREIGN PATENT DOCUMENTS

| | | | |
|---|---|---|---|
| EP | 0702973 | A2 | 3/1996 |
| EP | 2139543 | A1 | 1/2010 |
| FR | 2612401 | A1 | 9/1988 |
| FR | 2616331 | A1 | 12/1988 |
| FR | 2616665 | A2 | 12/1988 |
| JP | 02-046861 | A | 2/1990 |
| JP | 08-107933 | A | 4/1996 |
| JP | H11-512016 | A | 10/1999 |
| JP | 2005-021247 | A | 1/2005 |
| JP | 2010524646 | T | 7/2010 |
| WO | 9507722 | A1 | 3/1995 |
| WO | 9526764 | A1 | 10/1995 |
| WO | 9709077 | A1 | 3/1997 |
| WO | 9741907 | A2 | 11/1997 |
| WO | 2004071560 | A1 | 8/2004 |
| WO | 2006052737 | A1 | 5/2006 |
| WO | 2007026164 | A2 | 3/2007 |
| WO | 2008131440 | A1 | 10/2008 |
| WO | WO 2008/131440 A1 * | 10/2008 | ............ A61M 5/32 |
| WO | 2010064211 | A2 | 6/2010 |
| WO | 2010077596 | A1 | 7/2010 |
| WO | 2010087524 | A2 | 8/2010 |
| WO | 2011011697 | A1 | 1/2011 |
| WO | 2011112916 | A1 | 9/2011 |

OTHER PUBLICATIONS

International Search Report Issued Mar. 29, 2010 in Int'l Application No. PCT/US2009/066960.

Int'l Search Report issued Oct. 27, 2010 in Int'l Application No. PCT/US2010/043071; Written Opinion.

Int'l Search Report issued on Sep. 16, 2008 in Int'l Application No. PCT/US08/61331; Written Opinion.

Int'l Preliminary Report on Patentability Issued Aug. 14, 2009 in Int'l Application No. PCT/US08/61331.

(56) References Cited

OTHER PUBLICATIONS

Int'l Search Report issued on Mar. 23, 2006 in Int'l Application No. PCT/US05/39979.
Int'l Preliminary Report on Patentability Issued May 8, 2007 in Int'l Application No. PCT/US05/039979; Written Opinion.
U.S. Appl. No. 13/057,006 filed Feb. 1, 2011.
U.S. Appl. No. 60/928,423 filed May 10, 2007.
Int'l Preliminary Report on Patentability issued Jun. 14, 2011 in Int'l Application No. PCT/US2009/066960.
Office Action issued Mar. 2, 2012 in U.S. Appl. No. 12/597,103.
Int'l Preliminary Report on Patentability issued Apr. 9, 2012 in Int'l Application No. PCT/US10/43071.
Office Action issued May 15, 2012 in JP Application No. 2010-506461 (with English translation of relevant portions).
International Search Report Issued Aug. 4, 2011 in Int'l Application No. PCT/US2011/028072.
Office Action issued Aug. 10, 2012 in U.S. Appl. No. 12/597,103.
Office Action issued Aug. 2, 2013 in U.S. Appl. No. 13/057,006 by Tsals.
U.S. Appl. No. 13/870,330 by Evans, filed Apr. 25, 2013.
Office Action issued Apr. 30, 2013 in JP Application No. 2012-521832.
Office Action issued Mar. 14, 2013 in U.S. Appl. No. 12/597,103.
Office Action issued Apr. 15, 2013 in U.S. Appl. No. 13/057,006.
Office Action issued Nov. 26, 2013 in JP Application No. 2012-521832.
Office Action issued Jan. 6, 2014 in U.S. Appl. No. 13/057,006 by Tsals.
Office Action issued Dec. 17, 2013 in EP Application No. 11 710 607.0.
Office Action issued Apr. 8, 2014 in CN Application No. 201180013752.6.
Office Action issued Apr. 11, 2014 in U.S. Appl. No. 13/386,099 by Tsals.
English translation of an Office Action issued Apr. 11, 2014 in CN Application No. 201080041235.5.
Office Action issued May 5, 2014 in CN Application No. 200980148920.5.
Int'l Search Report and Written Opinion issued May 27, 2014 in Int'l Application No. PCT/US2014/019907.
Office Action issued Jul. 7, 2014 in CN Application No. 200980148920.5.
English translation of an Office Action issued Sep. 29, 2014 in CN Application No. 201080041235.5.
Office Action issued Nov. 6, 2014 in U.S. Appl. No. 13/386,099 by Tsals.
Office Action issued Jan. 14, 2014 in U.S. Appl. No. 13/355,031 by Tsals.
Extended European Search Report issued Sep. 8, 2014 in EP Application No. 08746707.2.
Office Action issued Apr. 16, 2015 in U.S. Appl. No. 13/870,330 by Evans.
Office Action issued Sep. 18, 2015 in U.S. Appl. No. 13/870,330 by Evans.
Int'l Preliminary Report on Patentability issued Sep. 17, 2015 in Int'l Application No. PCT/US2014/019907.
Office Action issued Dec. 16, 2015 in EP Application No. 08746707.2.

* cited by examiner

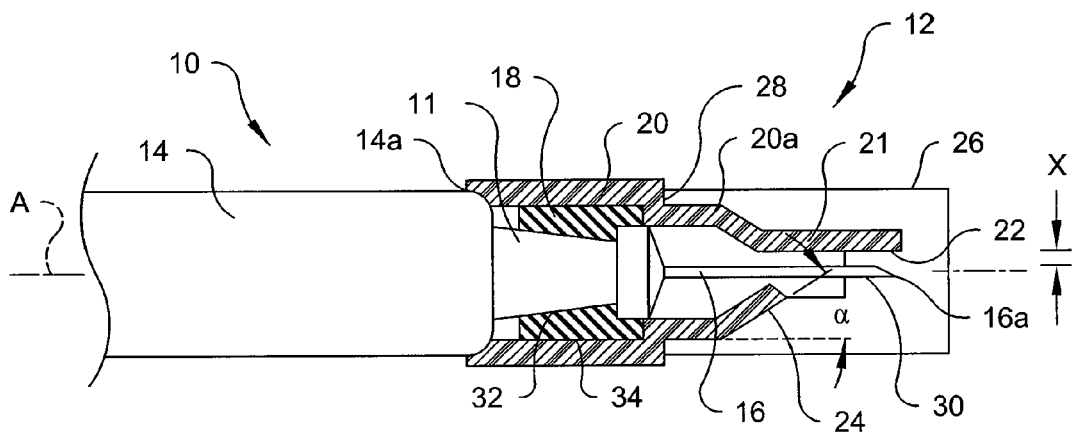
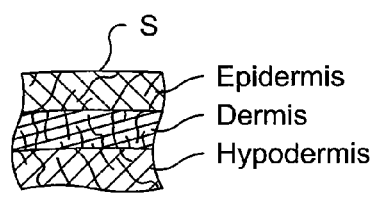
Fig. 1A
Fig. 1B
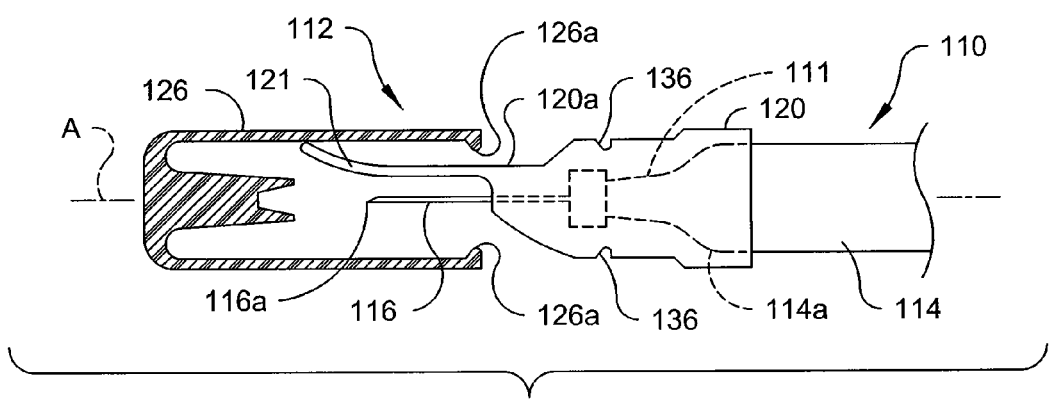
Fig. 2A
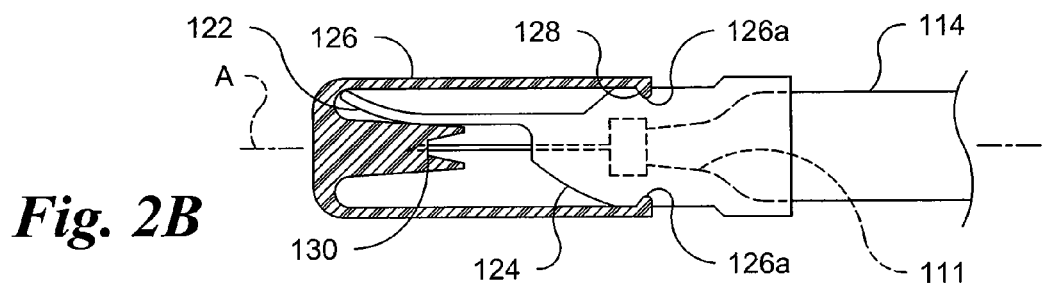
Fig. 2B

*Fig. 2C*
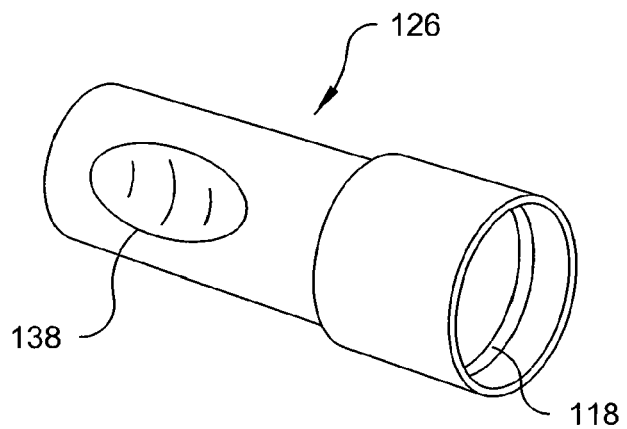
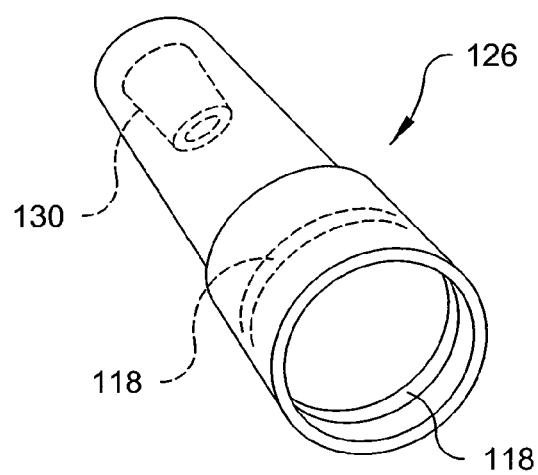
*Fig. 2D*
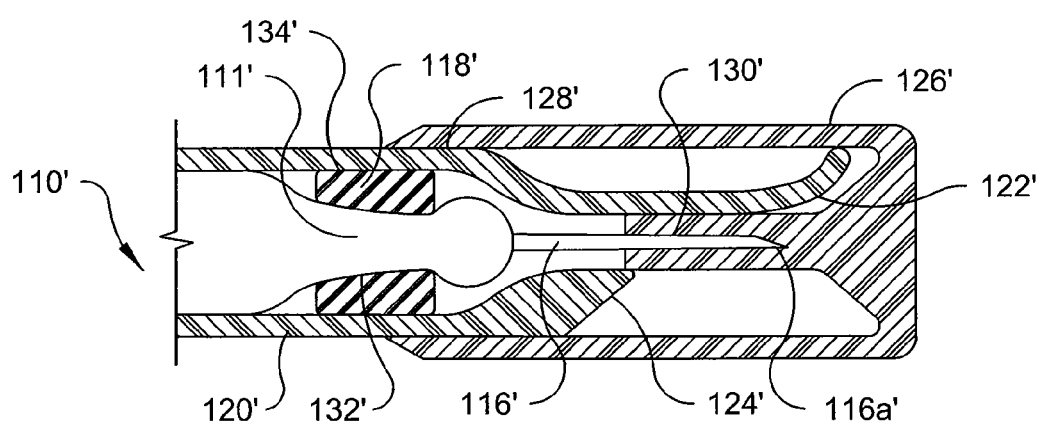
*Fig. 2E*

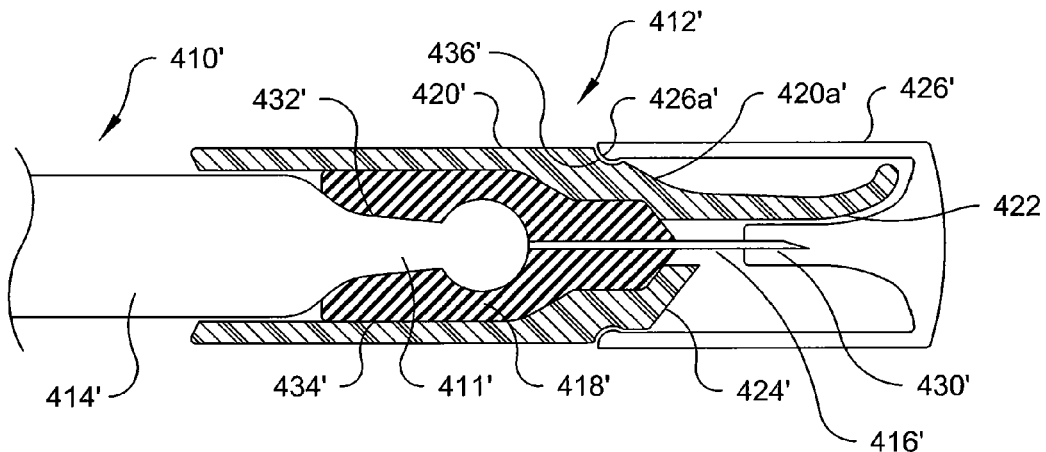
*Fig. 5C*
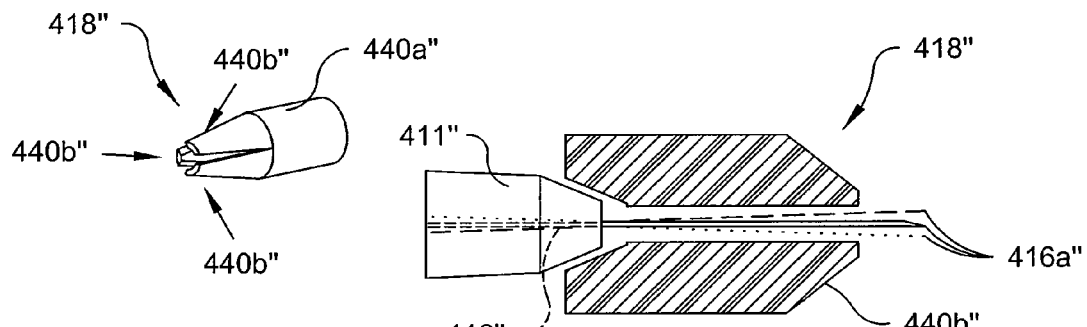
*Fig. 5D*  *Fig. 5F*
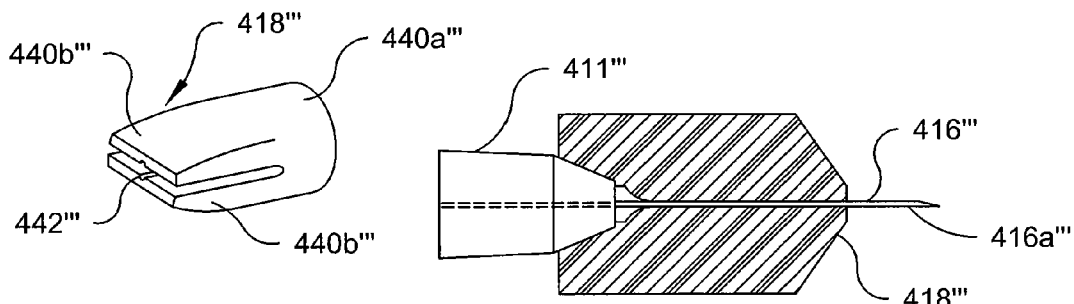
*Fig. 5E*  *Fig. 5G*

NEEDLE SHIELD AND ADAPTER FIXEDLY ATTACHED TO SYRINGE

CROSS-REFERENCE TO RELATED APPLICATION

This application is a section 371 of International Application No. PCT/US2011/028072, filed Mar. 11, 2011, which was published in the English language on Sep. 15, 2011 under International Publication No. WO 2011/112916 which claims the benefit of U.S. Provisional Patent Application No. 61/339,933, filed Mar. 12, 2010, the disclosures of which are incorporated herein by reference.

BACKGROUND OF THE INVENTION

The present invention is generally directed to an assembly for use with a syringe and, more particularly, to a combination of a syringe and an assembly having a sealing element, an adapter and a needle shield.

Intradermal ("ID") injections are used for delivering a variety of diagnostic and treatment compositions into a patient. ID injections are typically injections of a relatively small amount of medicament into the dermis, the dermal layer or even into a lower portion of the epidermis of a patient's skin (FIG. 1B). Substances may be injected intradermally for diagnostic testing, such as to determine a patient's immunity status against tuberculosis and the status of allergic diseases. Vaccines, drugs and other compounds may also be delivered intradermally. In many instances, ID delivery is preferred because it generally requires a smaller volume dose of the diagnostic compound or vaccine than other delivery techniques.

There is considerable variation in the thickness of a patient's skin, both between individuals and within the same individual at different sites of the body. Generally the outer skin layer, or the epidermis, typically has a thickness between two hundred and five hundred microns (200-500 µm) and the dermis, the inner and thicker layer of the skin, generally has a thickness between one and one-half to three and one-half millimeters (1.5-3.5 mm).

Administering an ID injection can be difficult and generally requires an experienced nurse or medical professional. Incorrect placement of the tip of a cannula or needle may lead to a failed injection. The placement of the cannula tip deeper than about three millimeters (3.0 mm) has the potential of delivering the injection into the subcutaneous region, where the ID dosage may be insufficient. Incorrect placement of the cannula may also puncture the skin again after being inserted into the dermis, with the delivered compound being lost on the surface of the skin. Injection is often followed by a jet effect, with the compound exiting the injection site through the puncture track. The jet effect is even more pronounced for injections through a cannula placed perpendicular to the injection site and in particular for shallow delivery.

The success of ID injections is often determined by the skill and experience of the individual healthcare professional administering the injection. A preferred ID injection technique (using a standard cannula) typically requires a healthcare professional to stretch the patient's skin, orient the cannula bevel to face upwardly, and insert a short bevel cannula at an angle of around ten to fifteen degrees)(10-15° relative to a surface of the skin, while also assuring that two to three millimeters (2-3 mm) of the cannula are located in the skin. The cannula tip ideally ends up positioned in the dermis or close to the dermis/epidermis boundary. The compound or medicament is slowly injected into the skin of the patient, forming a blister or wheal. The insertion of the cannula at an incorrect angle and/or depth results in a failed ID injection, which is typically repeated, causing additional pain and discomfort to the patient, as well as ineffective treatment to the patient. ID injection has been considered for immunization in the past, but has generally been rejected in favor of more reliable intramuscular or subcutaneous routes of administration because of the difficulty in making a successful ID injection, particularly when the injections are administered by relatively unskilled healthcare professionals.

Administration into the region of the ID space has been routinely used in the Mantoux tuberculin test, in which a purified protein derivative is injected at a shallow angle to the skin surface using a twenty-seven (27) gauge cannula and a standard syringe. The technique is known to be quite difficult to perform and generally requires specialized training. A degree of imprecision in the placement of the injection results in a significant number of false negative test results. ID injections are generally limited in volume to about 0.1 milliliter (ml), which is not enough for many common drugs. The difference with a subcutaneous injection (SQ) is only in the depo effect when a therapeutic compound is considered. ID is more effective for vaccines. Prior to injection, all needles are open and exposed either for IM, SQ or ID. ID has a shorter needle protected on one side by the adapter.

Therefore, it would be desirable to design and manufacture a syringe integral with ID adapter that allows a healthcare professional to provide a relatively simple, reliable ID injection, is relatively easy to use, is relatively cost effective to the user, limits waste of medicament, preserves a cannula closure prior to use and provides sterility of the cannula shaft and adapter sections contacting the patient skin. The devices and methods of the present invention accomplish the above objectives.

BRIEF SUMMARY OF THE INVENTION

Briefly stated, one aspect of a preferred embodiment of the present invention is directed to an assembly for use with a syringe having a barrel and a needle extending from a distal end thereof. The assembly includes a sealing element at least partially surrounding and positioned over at least a portion of the distal end of the syringe. An adapter that at least partially surrounds the sealing element is positioned over the distal end of the syringe. The adapter has a first skin contacting surface positioned at a distal end of the adapter. At least a portion of the first skin contacting surface extends generally parallel to at least a terminal end of the needle. The adapter also has a second skin contacting surface positioned proximally relative to the terminal end of the needle and at an angle to the first skin contacting surface. A needle shield at least partially surrounds and is removably positioned over at least one of the adapter, the sealing element and the syringe barrel.

In another aspect, a preferred embodiment of the present invention is directed to a combination of a syringe and an assembly. The syringe includes a barrel and a needle extending from a distal end thereof. The assembly includes an adapter positioned over at least a portion of the distal end of the syringe. The adapter has a first skin contacting surface positioned at the distal end of the adapter. At least a portion of the first skin contacting surface extends generally parallel to at least a terminal end of the needle. The adapter further has a second skin contacting surface positioned proximally relative to the terminal end of the needle and at an angle to the first skin contacting surface. A needle shield at least partially surrounds and is removably positioned over at least one of the adapter and the syringe barrel.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1A is a partial cross-sectional elevation view of a portion of a pre-filled syringe and an assembly according to a first preferred embodiment of the present invention shown in a first or combined configuration, wherein a sealing element and an adapter are shown in cross-section;

FIG. 1B is a cross-sectional view of the patient's skin taken from within box 1B of FIG. 4B;

FIG. 2A is a partial cross-sectional elevation view of a portion of a pre-filled syringe and an assembly according to a second preferred embodiment of the present invention shown in a second or separated configuration, wherein a needle shield is shown in cross-section;

FIG. 2B is a partial cross-sectional elevation view of the syringe and assembly shown in FIG. 2A in the first or combined configuration;

FIG. 2C is a perspective view of a portion of the assembly shown in FIG. 2B;

FIG. 2D is a perspective view of the portion of the assembly shown in FIG. 2C, with interior portions shown in phantom or broken lines for clarity;

FIG. 2E is a partial cross-sectional elevation view of a modified version of the syringe and assembly shown in FIGS. 2A and 2B;

FIG. 5C is a partial cross-sectional elevation view of the syringe and assembly shown in FIG. 5A, wherein the syringe and assembly are shown in the first or combined configuration and the sealing element and the adapter are shown in cross-section;

FIG. 5D is a perspective view of a portion of the assembly shown in FIGS. 5A-5C;

FIG. 5E is a partial cross-sectional elevation view of a portion of the syringe and a portion of the assembly shown in FIGS. 5A-5D, wherein the sealing element is shown in a natural or expanded configuration;

FIG. 5F is a perspective view of a modified version of the portion of the assembly shown in FIG. 5D;

FIG. 5G is a partial cross-sectional elevation view of a portion of the syringe and a portion of the assembly shown in FIG. 5E;

DETAILED DESCRIPTION OF THE INVENTION

Figure 3:
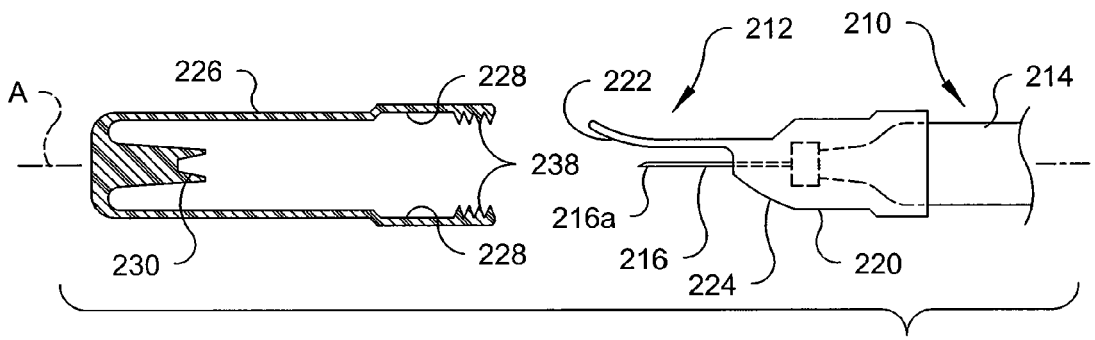
FIG. 3 is partial cross-sectional elevation view a portion of a pre-filled syringe and an assembly according to a third preferred embodiment of the present invention shown in the second or separated configuration, wherein a sealing element, an adapter and a needle shield are shown in cross-section.

Certain terminology is used in the following description for convenience only and is not limiting. The words "right" and "lower" designate directions in the drawings to which reference is made. The words "inwardly," "outwardly," "proximally" and "distally" refer to directions toward and away from, respectively, the geometric center or orientation of the assembly, the syringe or other related parts thereof. The words "connect," "connectable" and "connected" mean joined or linked together, either by direct engagement or through intermediate components. Unless specifically set forth herein, the terms "a," "an" and "the" are not limited to one element, but instead should be read as meaning "at least one." The terminology includes the above-listed words, derivatives thereof and words of similar import.

Referring to the drawings in detail, wherein like numerals indicate like elements throughout the views, FIG. 1A shows a first preferred embodiment of a combination of a syringe 10 and an assembly 12 for use therewith. While reference is made herein specifically to a pre-filled syringe 10, it is understood that the present invention is not so limited. For example, the assembly 12 described in detail below may also be used with nearly any type of syringe, such as those to be filled by a patient or user, for example. The assembly 12 is preferably designed for intradermal (ID) injection and at least portions thereof may be removably mounted or connected to at least a portion of the syringe 10. However, the assembly 12 is not limited to use only for ID injections. The assembly 12 may be removably positioned over or removably mountable to the syringe 10, or only a portion of the assembly 12 may be removably mountable to the syringe 10. For example, a portion of the assembly 12 may be fixedly mounted to a portion of the syringe 10, while a remaining portion or portions of the assembly 12 is/are removably attachable to the combination thereof.

The syringe 10 preferably includes a barrel 14, a plunger 515 with a piston 515a (none shown in FIG. 1A, but see the embodiment shown in FIG. 6B) slidable and sealingly engaged within a hollow cavity of the barrel 14. A needle or cannula 16 preferably extends outwardly from a distal end or hub 11 of the barrel 14 and is preferably fixedly attached thereto. The barrel 14 preferably has a generally cylindrical configuration in cross-section and the hollow internal cavity thereof preferably receives medicament (none shown) therein. The barrel 14 may be formed of glass, but the present invention is not so limited, as the barrel 14 may be formed of nearly any material, such as plastic or a polymer, capable of safely enclosing medicament. The medicament is preferably stored between a distal surface of the piston 515a and a proximal end (not shown in FIG. 1) of the needle 16 in the hollow internal cavity of the barrel 14. The hub 11 of the syringe 10 preferably includes an opening (not shown) that extends generally perpendicular to a longitudinal axis A of the combined syringe 10 and assembly 12 for receiving and/or capturing the proximal end of the needle 16. The syringe 10 is not limited to inclusion of the barrel 14, the plunger 515 and the needle 16, but may be comprised of nearly any device that is able to retain medicament therein, be joined with the assembly 12 and expel medicament therefrom, or otherwise inject medicament into a dermal layer of patient's skin S (see FIGS. 1B and 4B) in operation. For example, the needle 16 may be fixedly attached to either one of the syringe 10 or assembly 12, in which case a luer connection may be utilized.

In the first preferred embodiment, the assembly 12 preferably includes a sealing element 18 that at least partially surrounds and may be removably connectable to or positionable on or over at least a portion of the distal end or hub 11 of the barrel 14 or syringe 10. It is possible that the sealing element 18 is generally fixed to the hub 11 once the sealing element 18 is mounted thereto, such that it may be necessary to at least partially tear, destroy or brake the sealing element 18 to remove the sealing element 18 from the syringe 10. As shown in FIG. 1A, an outer or exterior surface of the sealing element 18 may be flat or planar in cross-section, while an opposing inner or interior surface of the sealing element 18 may be tapered downwardly or inwardly. The sealing element 18 preferably surrounds at least a portion of the distal end 11 of the barrel 14 or syringe 10 for a pre-determined length or distance along the longitudinal axis A of the syringe 10. The sealing element 18 also preferably extends around or surrounds an entire outer periphery or circumference of the distal end 11 of the syringe 10. The sealing element 18 is preferably formed of a rubber or a polymeric material, but is not limited to be constructed of only rubber or polymers.

An outer periphery or an outer circumference of the barrel 14 of the syringe 10 preferably extends radially outwardly (i.e., a direction generally perpendicularly to the longitudinal axis A) further than an outer periphery of the sealing element 18 when the sealing element 18 is compressed against the hub 11 (see FIG. 1). Thus, the outer periphery or the outer circumference of the sealing element 18 is preferably smaller or less than that of the barrel 14 of the syringe 10. In addition, FIG. 1A shows that a distal-most end or tip of the distal end 11 of the barrel 14 or syringe 10 extends axially along the longitudinal axis A further than a distal-most (right-most in FIG. 1A) end of the sealing element 18. However, the present invention is not limited to this configuration.

In the first preferred embodiment, the assembly 12 includes an adapter 20 that at least partially surrounds the sealing element 18 and may be removably positionable over or connectable to the distal end 11 of the syringe 10. It is possible that the adapter 20 is generally fixed and permanently attached to the distal end 11 of the syringe 10 once the adapter 20 is mounted thereto, such that it is necessary to at least partially tear, destroy or break the adapter 20 to remove the adapter 20 from the syringe 10. As shown in FIG. 1A, the adapter 20 preferably completely surrounds the entire outer periphery of the sealing element 18. Further, the adapter 20 preferably extends axially outwardly beyond each opposing lateral end or side of the sealing element 18 along the longitudinal axis A. The adapter 20 preferably includes a reduced diameter portion 20a proximate a distal end thereof. A distal protrusion 21, which forms at least a portion of the reduced diameter portion 20a, has a first skin contacting surface 22 and is preferably positioned at a distal end of the adapter 20. As shown in FIG. 1A, the distal protrusion 21 is preferably flat or planar in cross-section such that the distal protrusion 21 extend at least generally parallel to the longitudinal axis A, but the distal protrusion 21 may alternatively be at least partially curved or arcuate.

The first skin contacting surface 22 preferably faces at least a portion of the needle 16. As shown in FIG. 1A, it is preferred that at least a portion of the first skin contacting surface 22 extends generally parallel to at least a terminal end or distal tip 16a of the needle 16 and, therefore, generally, if not exactly, parallel to the longitudinal axis A. In addition, at least a portion of the first skin contacting surface 22, such as a distal-most portion thereof, preferably extends axially outwardly along the longitudinal axis A beyond the distal tip 16a of the needle 16.

In an injecting position (such as that shown in FIG. 4B), the first skin contacting surface 22 preferably directly contacts or engages the top surface of the patient's skin S to position the tip 16a of the needle 16 at a pre-determined depth into the skin S. In the injecting position, the tip 16a of the needle 16 is preferably positioned in the dermis or dermal layer of the skin S and the medicament is injected into the dermal layer for absorption. The generally continuous and preferably flat or planar first skin contacting surface 22 generally controls the distance between the tip 16a of the needle 16 and the patient's skin S to increase the likelihood that the tip 16a is properly positioned in the dermal layer in the injecting position.

At least an outer or exterior-most portion of a distal end of the needle 16, such as the distal tip 16a, is preferably spaced at a pre-determined distance X ("cannula gap distance") from above or below (depending upon the rotational position or orientation of the syringe 10) the first skin contacting surface 22. The cannula gap distance X is preferably at least two tenths of a millimeter (0.2 mm) and may be within a range of two tenths of a millimeter to two millimeters (0.2-2.0 mm). However, the cannula gap distance X is not limited to being in the above range and may include nearly any distance that permits the distal tip 16a of the needle 16 to be positioned in the dermal layer of the patient's skin S in the injecting position. In the first preferred embodiment, the cannula gap distance X is approximately fifty-five hundredth of a millimeter (0.55 mm). In addition, a more preferred range for the cannula gap distance X is approximately four tenths of a millimeter to eight tenths of a millimeter (0.4-0.8 mm). The cannula gap distance X may be impacted or modified by the orientation of the needle 16 (lancet up or lancet down), the gauge of the needle 16, the expected location of injection in the patient's skin S and numerous other factors that may be considered by the designer.

In addition, the adapter 20 preferably includes a second skin contacting surface 24 positioned proximate to the terminal end or distal tip 16a of the needle 16 and at a predetermined angle α with respect to the first skin contacting surface 22. The second skin contacting surface 24 is preferably sized and shaped to smoothly slide along the patient's skin S in the injecting position. In the injecting position, the second skin contacting surface 24 is preferably positioned below the needle 16. In the first preferred embodiment, the second skin contacting surface 24 defines a plane that preferably extends at an angle α, such as approximately 45 degrees, with respect to a plane defined by the first skin contacting surface 22 and the longitudinal axis A. The second skin contacting surface 24 may be flat or planar, or the second skin contacting surface 24 may be arcuate or slightly curved, or even have a portion that is generally linear and additional portions that are arcuate and/or curved.

In the first preferred embodiment, the assembly 12 further includes a cover or needle shield 26 that at least partially surrounds and is preferably removably connectable or positionable over at least one of the adapter 20, the sealing element 18, and the barrel 14 of the syringe 10. The needle shield 26 is preferably a cover or enclosure to protect and/or enclose at least the distal tip 16a of the needle 16 and/or the first and second skin contacting surfaces 22, 24 of the adapter 20. The needle shield 26 preferably includes a completely closed distal end and an opposing open proximal end. In the first preferred embodiment, the needle shield 26 is also preferably sized and shaped to enclose and/or surround at least the reduced diameter portion 20a of the adapter 20. However, the needle shield 26 may be sized and shaped to surround and/or cover the entire outer periphery of the adapter 20. The needle shield 26 may be formed of a rigid polymeric material and a rubber material, for example.

As shown in FIG. 1A, the needle shield 26 may be positioned in a first, attached or connected configuration with at least one of the adapter 20, the sealing element 18, and the barrel 14 of the syringe 10. In this first configuration, at least a portion of the needle shield 26 preferably directly engages and/or surrounds at least a portion of the distal tip 16a of the needle 16, such that the tip 16a of the needle 16 is sealed and/or held in a single, defined location by the needle shield 26. The needle shield 26 may be designed so that at least a distal tip 16a of the needle 16 punctures at least a portion of an interior of the needle shield 26 in the first configuration. An interior surface of the needle shield 26 may also directly engage the second skin contacting surface 24 in the first configuration and seal the needle shield 26 against the reduced diameter portion 20a of the adapter 20. An outer periphery of the adapter 20 may extend radially outwardly perpendicular to the longitudinal axis A at least slightly further than an outer periphery of the needle shield 26. Further, at least a portion of the distal protrusion 21 of the adapter 20 is directly engaged and/or surrounded by an interior of the needle shield 26, such that at least a distal end of the distal protrusion 21 is held in a single, defined location by the needle shield 26 in the first configuration.

As is understood by those skilled in the art, the needle shield 26 also preferably includes a second or at least partially separated configuration (not shown in FIG. 1A, but see FIG. 2A for example) in which the needle shield 26 is spaced a predetermined distance apart or away from at least one of the adapter 20, the sealing element 18 and the barrel 14 of the syringe 10 along the longitudinal axis A. In the injecting position (i.e., the second configuration), the needle shield 26 is removed from at least one of the adapter 20, the sealing element 18 and the barrel 14 of the syringe 10.

Referring to FIG. 1A, in the first or assembled configuration of the syringe 10 and assembly 12, the sealing element 18 is preferably at least partially compressed to seal the adapter 20 to at least a portion of the hub 11 of the barrel 14 or syringe 10. However, compression may not be required, as the respective structures may simply contact or engage one another. Further, at least a portion of the proximal end of the adapter 20 preferably contacts and/or engages at least a portion of the barrel 14 of the syringe 10 at a shoulder 14a of the barrel 14. The above-described connections preferably create a mechanical retention of the adapter 20 on the barrel 14. A first seal 28 is preferably formed between the needle shield 26 and the reduced diameter portion 20a of the adapter 20, a second seal 30 formed between the needle shield 26 and the terminal end 16a of the needle 16, a third seal 32 formed between the sealing element 18 and at least a portion of the syringe 10, such as the hub 11, and a fourth seal 34 formed between the adapter 20 and the sealing element 18. Each seal 28, 30, 32, 34 preferably forms a moisture and/or air-tight connection between respective structure or elements of the syringe 10 and the assembly 12. Thus, the seals 28, 30, 32, 34 preferably preserve and/or maintain the sterile nature of the needle 16 and the first and second skin contacting surfaces 22, 24 of the adapter 20 and seal the medicament in the syringe 10 in the assembled configuration (FIG. 1A), such that contaminants, such as bacteria, cannot reach the needle 16, for example, at least until the needle shield 26 is removed from the adapter 20.

The assembly 12 is preferably attached to or assembled with the pre-filled syringe 10 at the time of manufacture (specifically, prior to the filling process). At least a portion of the assembly 12 may be configured to be permanently affixed to or molded onto at least a portion of the syringe 10, such as by adhesive bonding. The assembly 12 is preferably used by healthcare professionals, but may also be used by non-healthcare professionals, potentially for self-injection and typically when the assembly 12 is pre-assembled to the syringe 10. The adapter 20, the sealing element 18 and the needle shield 26 may be provided in an assembled states as a sub-assembly ready for assembly with the syringe 10. The needle tip 16A is preferably sealed to prevent liquid in the barrel 14 of the syringe 10 from leaking out. The syringe 10 and the assembly 12 are preferably sterilized during the manufacturing process, and sterility is preferably maintained up to the time of use, which is accomplished by at least the first seal 30 between the syringe 16 and the needle shield 26 and, more preferably, by all of the seals 28, 30, 32, 34 of the present invention. The above-described features generally reduce the number of steps the user has to go through to prepare for ID injection. As a result, the possible mistakes that could be made, including incorrect cannula and adapter alignment, compromised sterility and wasted medicament, are also reduced.

Referring to FIGS. 2A-2E, various forms of a second preferred embodiment of the combination of a syringe 110 and assembly 112 is shown. The reference numerals of the second preferred embodiment are distinguishable from those of the first embodiment by a factor of one hundred (100), but otherwise indicate the same elements as indicated in the first preferred embodiment, except as otherwise specified. The syringe 110 and assembly 112 of the second preferred embodiment are substantially similar to those of the first preferred embodiment. Specific similarities between the two embodiment may be omitted herein for the sake of brevity and convenience, and therefore is not limiting.

In the second preferred embodiment, the needle shield 126 preferably surrounds and/or covers only a portion of the adapter 120, such that a length of the needle shield 126, as measured along the longitudinal axis A, is relatively short. The needle shield 126 is preferably formed of a rigid material and preferably includes one or more protrusions 126*a* (FIGS. 2A and 2B) that extend radially inwardly from a proximal end of the needle shield 126. The protrusion 126*a* preferably extends around an entire inner periphery or circumference of the needle shield 126 and is sized and shaped to engage one or more grooves or detents 136 in an exterior surface of the adapter 120. The protrusion 126*a* may extend continuously and uninterrupted around an interior circumference of the needle shield 126, or the protrusions 126*a* may be located at discrete, spaced-apart points along the interior circumference of the needle shield 126. Further, as shown in FIGS. 2C and 2D, the elastomer sealing element 118 may be formed on the interior circumference of the needle shield 126 at the open proximal end thereof, and preferably extends the entire circumference thereof. The sealing element 118, which is not shown in FIGS. 2A and 2B for clarity of other structure, is preferably directly connected to an integrally formed with the needle shield 126, and the sealing element 118 may be in addition to or in place of the protrusion(s) 126.

As shown in FIGS. 2A and 2B, the distal protrusion 121, which forms a portion of the reduced diameter portion 120*a* and includes the first skin contacting surface 122, is preferably at least partially curved or arcuate. More specifically, a distal tip of the distal protrusion 121 preferably curves upwardly and/or outwardly away from the longitudinal axis A, while a more proximate portion of the distal protrusion 121 is flat or planar and extends generally parallel to the longitudinal axis A. Accordingly, the interior of the needle shield 126 is sized and shaped to receive the arcuate distal protrusion 121 therein without damaging the distal protrusion 121. As compared to the first preferred embodiment, the needle shield 126 of the second preferred embodiment includes a sidewall of reduced thickness so as to create a larger, more open internal cavity to receive the arcuate distal protrusion 121 in any rotational position.

As shown in FIG. 2B, a first seal 128 may be formed at the connection of the protrusion 126 and the one or more grooves 136. As shown in FIGS. 2B and 2D, a second seal 130 on the interior of the needle shield 126 is formed between the needle shield 126 and a terminal and/or distal tip 116*a* of the needle 116. The second seal 130 preferably includes a distal end proximate an interior surface of the closed distal end of the needle shield 126 and an opposing proximal end that extends axially toward the open proximal end of the needle shield 126. The second seal 130 preferably includes an outer or exterior sidewall that tapers from the distal end to the proximal end thereof. A hole or depression is formed at the proximal end of the second seal 130 to receive the distal end 116*a* of the needle 116 therein in the first or assembled configuration (FIG. 2B). The second seal 130 may be inserted into the interior of the needle shield 126 or co-molded with the needle shield 126, such that the second seal 130 is formed integrally with the needle shield 126.

As shown in FIGS. 2C and 2D, the needle shield 126 is not limited to the inclusion of the protrusion 126*a*, as an interior surface of the proximal end of the needle shield 126 may be smooth or coplanar with at least the remaining portion of an interior of the needle shield 126. The third seal (not shown in FIGS. 2A and 2B for clarity of the remaining features) is preferably formed between an interior surface of the sealing element 118 and an exterior surface of the adapter 120. Alternatively, the third seal may be formed between an interior surface of the needle shield 126 distal of the protrusions 126*a* and an exterior surface of the adapter 120 distal of the grooves 136. As shown in FIG. 2C, an exterior surface of the needle shield 126 may include at least one and preferably two spaced-apart depressions or finger grips 138, which allow a user to more easily remove the needle shield 126 from the adapter 120.

FIG. 2E shows a modified version of the syringe 110' and assembly 112' the second preferred embodiment shown in FIGS. 2A-2D, wherein a prime symbol (') distinguishes like elements from the second preferred embodiment. As shown in FIG. 2E, the first seal 128' is formed between an interior surface of the needle shield 126' and an exterior surface of the adapter 120'. The needle shield 126' is preferably attached to the adapter 120' by friction or a friction fit. The second seal 130' is formed between the needle shield 126' and the terminal end 116*a*' of the needle 116'. The third seal 132' is formed between an interior surface of the sealing element 118' and an exterior surface of the hub 111" of the syringe 110'. The fourth seal 134' is formed between an exterior surface of the sealing element 118' and an interior surface of the adapter 120'.

FIG. 3 shows a third preferred embodiment of the combination of the syringe 210 and assembly 212 in the second or at least partially separated configuration. The reference numerals of the third preferred embodiment are distinguishable from those of the first embodiment by a factor of two hundred (200), but otherwise indicate the same elements as indicated in the first preferred embodiment, except as otherwise specified. The syringe 210 and the assembly 212 of the third preferred embodiment are substantially similar to those of the first and second preferred embodiments described above. Specific similarities between the embodiments may be omitted herein for the sake of brevity and convenience, and therefore, is not limiting.

Initially, the needle shield 226 preferably surrounds and/or covers the entire adapter 220 in the first or combined configuration (not shown in FIG. 3), such that a length of the needle shield 226, as measured along the longitudinal axis A, is relatively long as compared to that of the second preferred embodiment. Another distinguishing feature of the third preferred embodiment is that an interior surface of a proximal end of the needle shield 226 includes one or more gripping members 238 for directly engaging the barrel 214 of the syringe 210. The gripping member(s) 238 may be a single, continuous structure extending around an entire inner circumference of the needle shield 226, or may be a plurality of spaced-apart segments extending around at least a portion of the inner circumference of the needle shield 226. Further, a sealing element, such as the sealing element 18 described above for the first preferred embodiment, is not required in the third preferred embodiment.

In the third preferred embodiment, the first seal 228 is preferably formed at a surface of a flush engagement between an interior surface of the needle shield 226 and an exterior surface of the barrel 214, when the needle shield 226 is directly connected to the barrel 214 of the syringe 210. Thus, the needle shield 226 is preferably sized and shaped to receive the entire adapter 220 therein, such that in the first configuration, the gripping member(s) 238 is/are positioned proximate a proximal end of the adapter 220 along the longitudinal axis A. In the third preferred embodiment, the second seal 230, which is preferably similar in structure to the second seal 130 of the second preferred embodiment, is formed when the distal tip 216a of the needle 216 is embedded in an interior distal end of the needle shield 226. The gripping member(s) 238 may function as a sealing element integrally formed with the needle shield 226 and forming a third seal with an exterior surface of the barrel 214 of the syringe 210. Alternatively, the gripping member(s) 238 may form a fourth seal with an exterior surface of the adapter 220.

Referring to FIGS. 4A-D, a fourth preferred embodiment of the combination of the syringe 310 and assembly 312 is shown. Reference numerals of the fourth embodiment are distinguishable of those of the first preferred embodiment by a factor of three hundred (300), but otherwise indicate the elements of the first embodiment except as otherwise specified. The syringe 310 and assembly 312 of the fourth preferred embodiment are substantially similar to those of the previously described embodiments. Specific similarities between the embodiments may be omitted herein for the sake of brevity and convenience, and therefore is not limiting.

Figure 4A:
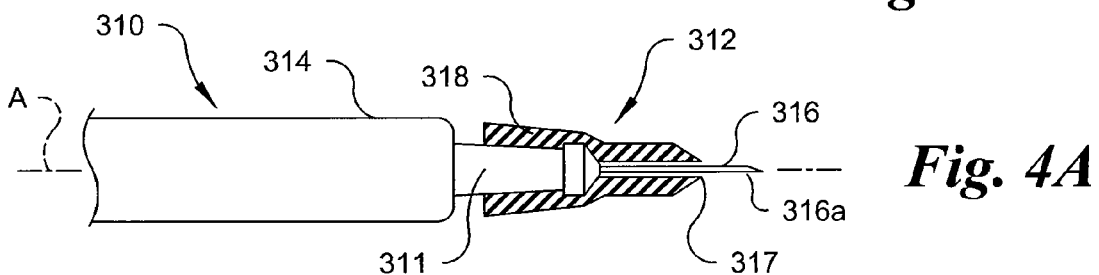
FIG. 4A is a partial cross-sectional elevation view of a portion of a pre-filled syringe and a portion of an assembly according to a fourth preferred embodiment of the present invention, wherein a sealing element is shown in cross-section.

In an unassembled state of the assembly 312 shown in FIG. 4A, the sealing element 318, which preferably surrounds at least a portion of the hub 311 of the barrel 314 and at least a portion of the needle 316, is in a partially relaxed or expanded state. In the partially expanded state, the portion of the sealing element 318 surrounding the needle 316 may not directly engage the needle 316, such that at least a portion of an interior surface of the sealing element 318 is spaced radially away from the needle 316 and the longitudinal axis A. Thus, a slight gap or spacing 317 may be located between the needle 316 and the sealing element 318. However, in a partially assembled configuration of the assembly 312 shown in FIG. 4B, the adapter 320 preferably surrounds the entire sealing element 318 and compresses the sealing element 318 to engage at least a portion of the needle 316. As a result, the sealing element 318 engages at least a portion of the needle 316, such as the proximal end thereof, and properly centers and/or aligns the needle 316 relative to the first skin contacting surface 322 of the adapter 320 in the injecting position (FIG. 4B).

Figure 4B:
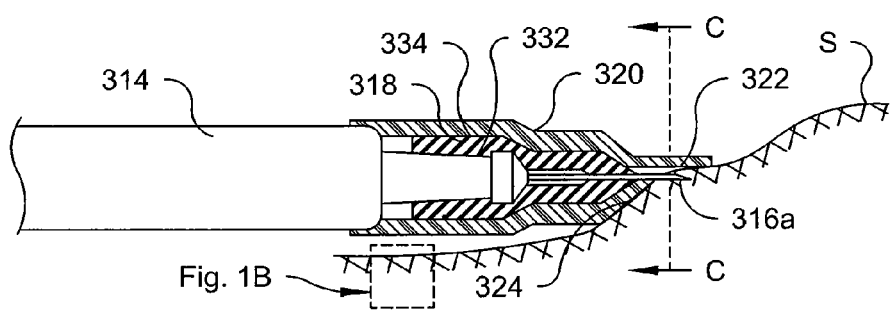
FIG. 4B is a partial cross-sectional elevation view of the pre-filled syringe shown in FIG. 4A with portions of the assembly attached thereto, wherein the syringe and assembly are shown in an injecting position.
Figure 4C:
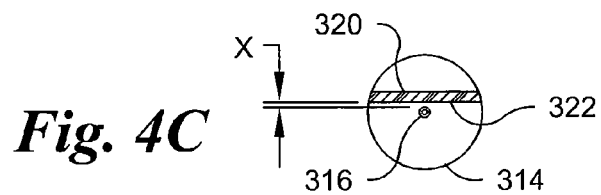
FIG. 4C is a front elevation view of the combined syringe and assembly of FIG. 4B taken along line C-C of FIG. 4B.
Figure 4D:
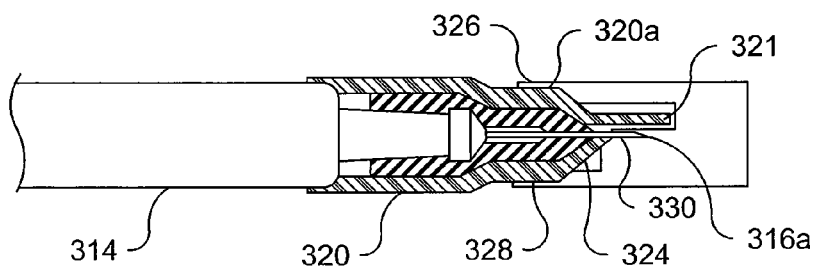
FIG. 4D is a partial cross-sectional elevation view of the pre-filled syringe shown in FIG. 4A with the entire assembly attached thereto, wherein a sealing element and adapter are shown in cross-section.

In the injecting position shown in FIG. 4B, the entire second skin contacting surface 324 and at least a portion of the first skin contacting surface 322 of the adapter 320 are preferably pressed directly against the patients skin S. FIG. 4C shows a front elevation view of the adapter 320 mounted to the barrel 314 of the syringe 310. As can be seen in FIG. 4C, the first skin contacting surface 322 is generally flat or planar and extends a pre-determined distance X ("cannula gap distance") above the needle 316. In the first or fully connected or assembled configuration in FIG. 4D, the needle shield 326 generally surrounds and/or encloses at least the distal tip 316a of the needle 316 and the reduced diameter proportion 320a of the adapter 320. In the fully assembled configuration shown in FIG. 4D, the first seal 328 is formed between an interior surface of the needle shield 326 and an exterior surface of the adapter 320. The second seal 330 is formed between an interior portion of the needle shield 326 and at least a portion of the terminal end 316a of the needle 316. The third seal 332 (FIG. 4B) is formed between the sealing element 318 and the hub 311 of the syringe 310. The fourth seal 334 (FIG. 4B) is formed between the adapter 320 and the sealing element 318.

Referring to FIGS. 5A-5G, various forms of a fifth preferred embodiment of the combination of the syringe 410 and the assembly 412 are shown. The reference numerals of the fifth preferred embodiment are distinguishable from those of the first preferred embodiment by a factor of four hundred (400), but otherwise indicate the same elements as indicated in the first preferred embodiment, except as otherwise specified. The syringe 410 and the assembly 412 of the fifth preferred embodiment are substantially similar to those of the first preferred embodiment. Specific similarities between the embodiments may be omitted herein for the sake of brevity and convenience, and therefore is not limiting.

The sealing element 418 of the fifth preferred embodiment preferably includes a uniform proximal end 440a and multiple segments 440b that extend therefrom and engage the proximal portion of the needle 416 in the compressed state. The multiple segments 440b are preferably separated and at least partially spaced-apart in an unstressed state. In operation, and prior to injection, the sealing element 418 is preferably slid over or installed onto at least a portion of the hub 411 of the barrel 414 or syringe 410. The adapter 420 is then preferably slid over or installed onto the exterior surface of the sealing element 418. Attachment of the adapter 420 to the sealing element 418 compresses the sealing element 418 from the relaxed or expanded state shown in FIG. 5A to the compressed or contracted state shown in FIG. 5C. The compression of the sealing element 418 supports and/or aligns the needle 416 in the proper position or orientation for injection. It is preferred that the needle shield 426 is then slid over or assembled onto the adapter 420 prior to injection. Similar to the second preferred embodiment, it is preferred that the open proximal end of the needle shield 426 includes one or more protrusions 426a that are sized and shaped to engage or be received by one or more grooves 436 formed in an exterior surface of the adapter 420. The combination of the protrusion(s) 426a and the groove(s) 436 creates a snap-fit connection when the needle shield 426 is attached to the adapter 420.

Figure 5A:
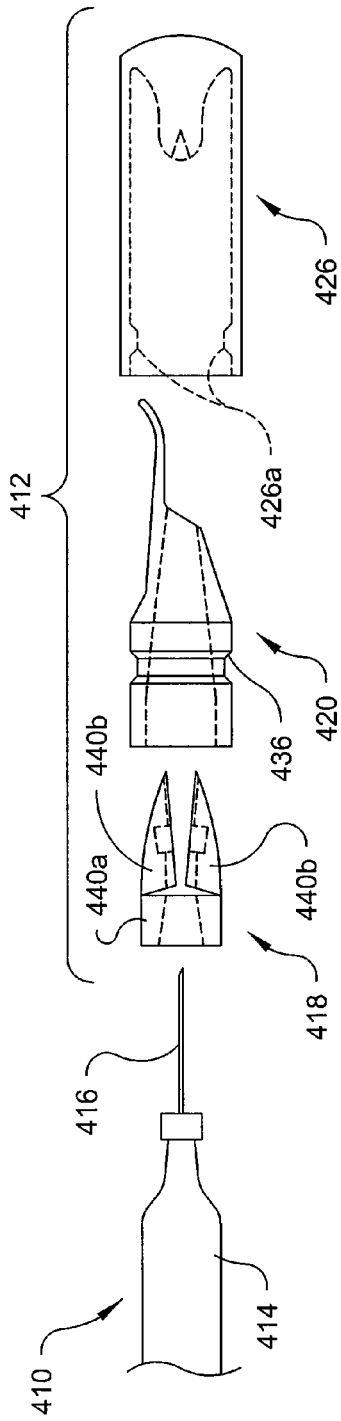
FIG. 5A is an exploded elevation view of a portion of a pre-filled syringe and an assembly according to a fifth preferred embodiment of the present invention shown in the second or separated configuration.
Figure 5B:
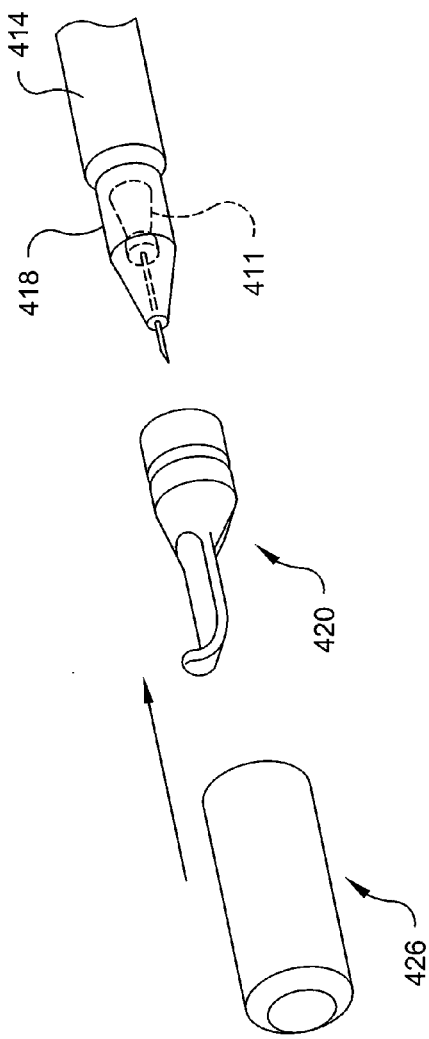
FIG. 5B is a partially exploded perspective view of a portion of the syringe and assembly shown in FIG. 5A.

FIGS. 5C-5G show three modified versions of the syringe 410' and assembly 412' of the fifth preferred embodiment shown in FIGS. 5A and 5B, wherein one or more prime symbols ('), (") or ('") distinguishes like elements from the fifth preferred embodiment. In the modified embodiment shown in FIG. 5C, the first seal is formed at the connection between the protrusion(s) 426a' and the groove(s) 436'. The protrusion(s) 426a' generally separate the reduced diameter portion 420a' of the adapter 420' from a proximal end of the adapter 420'. In the modified embodiment shown in FIGS. 5D and 5F, the sealing element 418" preferably includes multiple segments 440b" that directly engage the proximal portion of the needle 416a" in the compressed stated. Specifically, the sealing element 418" includes a generally uniform proximal end 440a" and three spaced-apart segments 440b" at the distal end thereof. Similarly, in the modified embodiment shown in FIGS. 5E and 5G, the sealing element 418''' preferably includes a generally uniform proximal end 440a''' and two spaced-apart segments 440b''' at the distal end thereof. Each segment 440b''' may include a centrally located detent or depression 442''' sized and shaped to receive at least a portion of the needle 416''' therein. As shown in FIG. 5G, the sealing element 418''' engages the proximal portion of the needle 416''' in the fully assembled operative configuration. Compression of the sealing element 418, 418', 418'', 418''' by the adapter 420, 420' prevents inadvertent or unintended movement or oscillation of the needle 416, 416', 416'', 416''', as depicted in FIG. 5F.

Referring to FIGS. 6A-6E, various forms of a sixth preferred embodiment of the combination of the syringe 510 and the assembly 512 are shown. The reference numerals of the sixth preferred embodiment are distinguishable from those of the first preferred embodiment by a factor of five hundred (500), but otherwise indicate the same elements as indicated in the first preferred embodiment, except as otherwise specified. The syringe 510 and the assembly 512 of the sixth preferred embodiment are substantially similar to those of the first preferred embodiment. Specific similarities between the embodiments may be omitted herein for the sake of brevity and convenience, and therefore is not limiting.

A distinguishing feature of the adapter 520 of the sixth preferred embodiment is that at least a portion of the first skin contacting surface 522 is non-linear, non-planar or eccentric in shape. More specifically, the first skin contacting surface 522 is non-linear in a plane that extends perpendicularly to a plane defined by the longitudinal axis A. Further, the adapter 520 includes a cut-out portion or opening 548, which preferably extends along the longitudinal axis A generally the entire length of the distal protrusion 521. The combination of the shape of the distal protrusion 521 and the cut-out portion 548 creates an arch (see FIG. 6A) at the distal-most end of the distal protrusion 521. The unique shape of the adapter 520 and the cut-out portion 548 provides sufficient clearance between the first skin contacting surface 522 and the needle 516 to allow for efficient and proper installation of the needle shield 526. In other words, the cut-out portion 548 and the shape of the first skin contacting surface 522 accommodates the needle shield 526 during installation. As shown in FIG. 6C, the needle shield 526 is preferably sized and shaped to fit within at least a portion of the adapter 520, such that an exterior surface of the needle shield 526 is adjacent to or in abutting contact with at least a portion of the first skin contacting surface 522 in the first or connected configuration. In other words, the adapter 520 generally surrounds the needle shield 526 in the first or connected configuration.

Referring again to FIG. 6C, the sixth preferred embodiment may include a second needle shield 526a (shown in phantom). The second needle shield 526a preferably surrounds the entire first or inner needle shield 526 and at least a portion of the adapter 520. The second needle shield 526a is preferably formed of a rigid polymer, but the outer or second needle shield 526a is not so limited. The second needle shield 526a preferably protects both the inner needle shield 526 and the adapter 520, and preferably maintains at least a portion of each in a sterile environment. The second needle shield 526a may be substantially similar to the needle shield 126 of the second preferred embodiment described above.

Figure 6A:
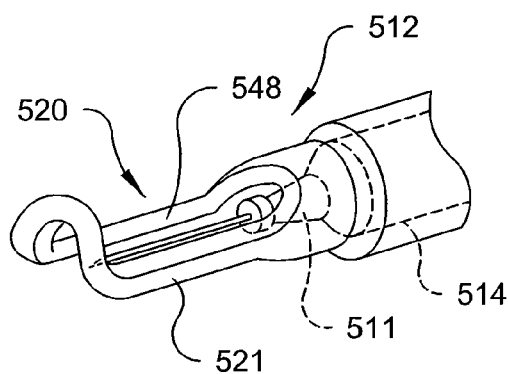
FIG. 6A is a perspective view of a portion of a pre-filled syringe and a portion of an assembly according to a sixth preferred embodiment of the present invention.
Figure 6B:
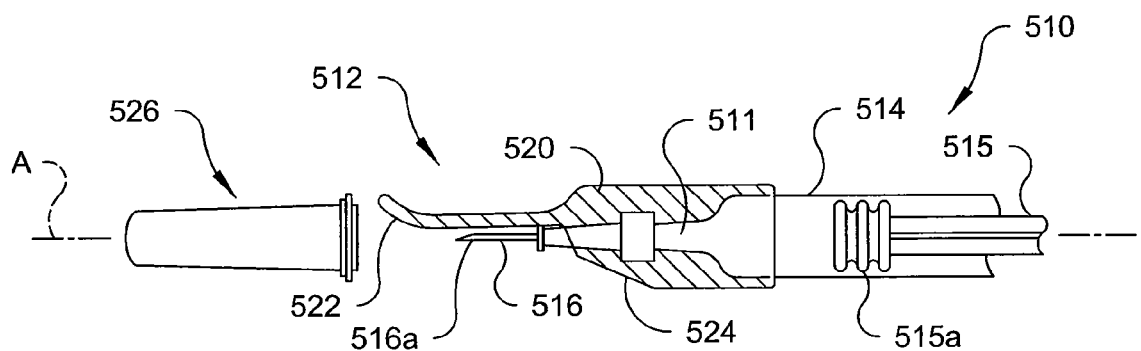
FIG. 6B is a partial cross-sectional elevation view of the syringe and assembly shown in FIG. 6A, wherein the syringe and assembly are shown in a partially second or separated configuration and an adapter is shown in cross-section.
Figure 6C:
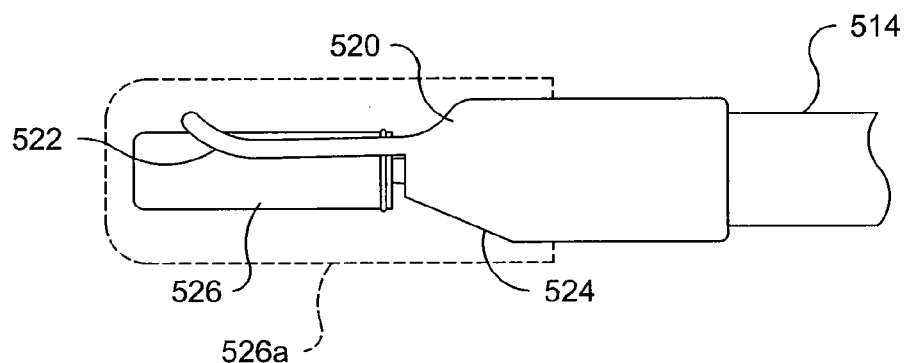
FIG. 6C is an elevation view of the syringe and assembly shown in FIG. 6B, wherein the syringe and assembly are shown in the first or combined configuration.
Figure 6D:
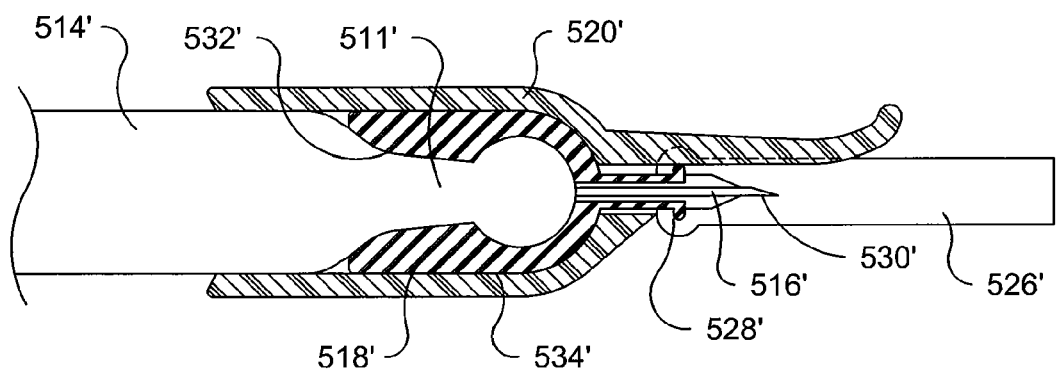
FIG. 6D is a partial cross-sectional elevation view of a modified version of the syringe and assembly shown in FIGS. 6B and 6C, wherein the syringe and assembly shown in the first or combined configuration and a sealing element and the adapter are shown in cross-section.
Figure 6E:
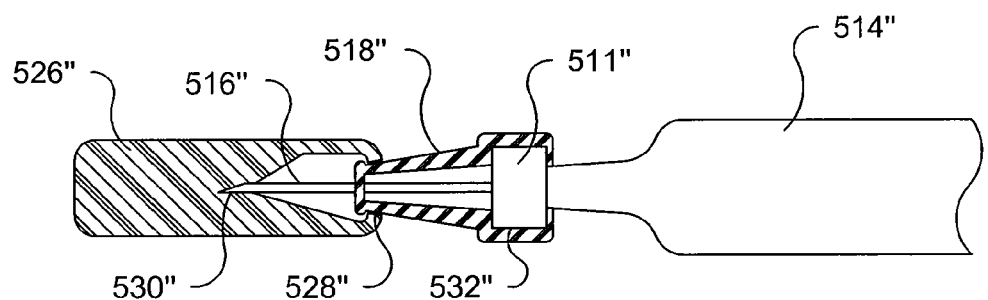
FIG. 6E is a partial cross-sectional elevation view of another modified version of the syringe assembly shown in FIG. 6D, wherein a needle shield is shown attached directly to the sealing element.

FIGS. 6D-6E show two modified versions of the syringe 510', 510'' and assembly 512', 512'' of the sixth preferred embodiment shown in FIGS. 6A-6C, wherein one or more prime symbols (') or ('') distinguishes like elements from the sixth preferred embodiment. In the modified versions, the needle shield 526', 526'' is directly connectable to or attachable to at least a portion of the sealing element 518', 518''. Thus, the first seal 528', 528'' may be formed by the connection of the needle shield 526', 526'' and the sealing element 581', 518''.

Referring to FIGS. 7A-7E, various forms of a seventh preferred embodiment of the combination of the syringe 610 and the assembly 612 are shown. The reference numerals of the seventh preferred embodiment are distinguishable from those of the first preferred embodiment by a factor of six hundred (600), but otherwise indicate the same elements as indicated in the first preferred embodiment, except as otherwise specified. The syringe 610 and the assembly 612 of the seventh preferred embodiment are substantially similar to those of the sixth preferred embodiment. Specific similarities between the embodiments may be omitted herein for the sake of brevity and convenience, and therefore is not limiting.

Figure 7A:
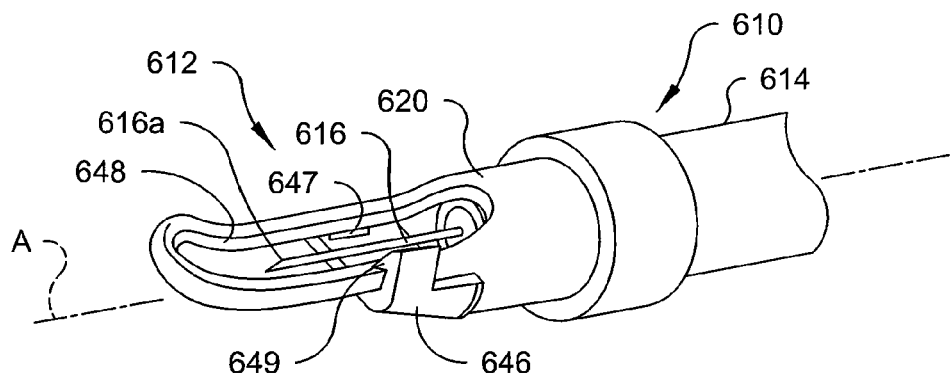
FIG. 7A is a perspective view of a portion of a syringe and a portion of an assembly according to a seventh preferred embodiment of the present invention shown in the first or combined configuration.

The seventh preferred embodiment preferably includes a hinged element 646 connected to the adapter 620. In an operative configuration, at least a portion of the hinged element 646 engages and/or provides support to a proximal portion of the needle 616. The hinged element 646 preferably includes a molded living hinge 647 at a point of connecting with the adapter 620. The hinged element 646 is preferably movable from a first or closed position (FIG. 7A) (i.e., operative configuration or shipping/storage position) for directly engaging, supporting and aligning the needle 616 to a second or open position (FIG. 7C) for accommodating the needle shield 626 attached directly to the hub 611 of the syringe 610 (see FIG. 7D). In the closed position shown in FIG. 7A, the hinged element 646 preferably extends from one lateral or radial side of the adapter 620 to an opposing lateral or radial side thereof, such that the hinged element 646 generally spans an entire width of the cut-out portion 648. An end of the hinged element 646 opposite the living hinge 647 preferably includes a hook or catch 649 for directly engaging and/or locking onto a portion of the adapter 620, so as to maintain the hinged element 646 in the closed position. Referring to FIG. 7A, a predetermined distance of a portion of a distal end of the needle 616, such as approximately four millimeters (4 mm), extends beyond a distal end of the hinged element 646 when the hinged element 646 is in the closed position.

Figure 7B:
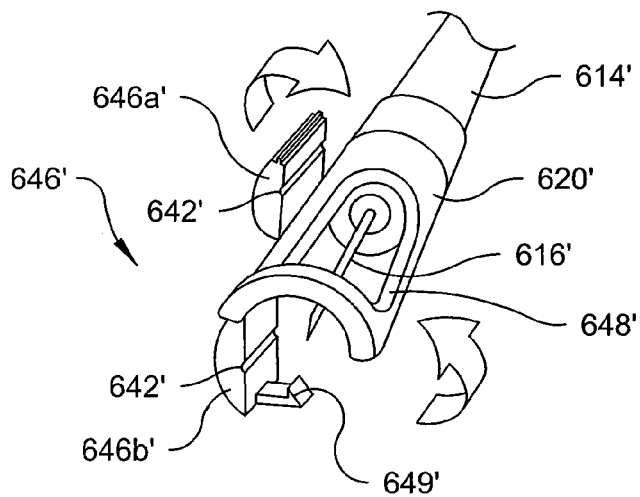
FIG. 7B is a perspective view of modified version of a portion of the syringe and a portion of the assembly shown in FIG. 7A.
Figure 7C:
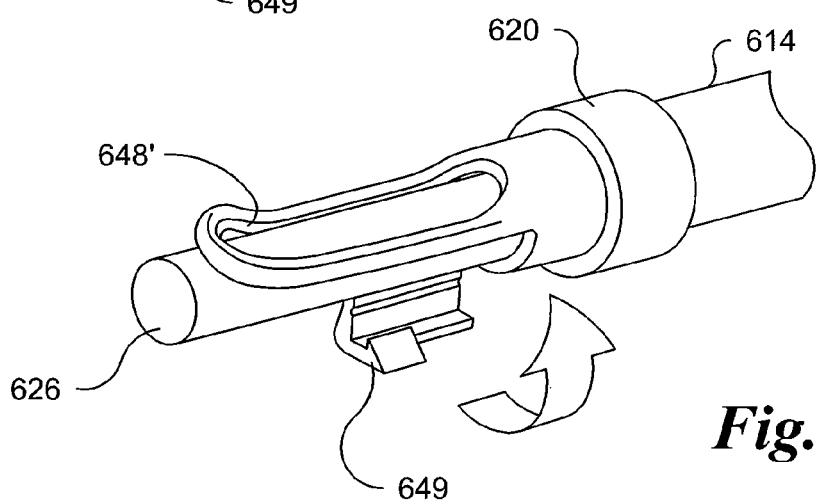
FIG. 7C is a perspective view of a portion of the syringe and the assembly shown in FIG. 7A, wherein the syringe and assembly are shown in the first or combined configuration.
Figure 7D:
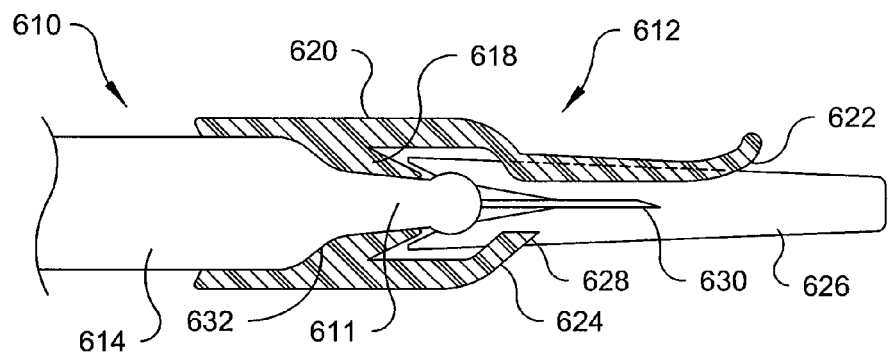
FIG. 7D is a partial cross-sectional elevation view of a portion of the syringe and the assembly shown in FIG. 7C, wherein an adapter is shown in cross-section.

FIG. 7B shows a modified version of the seventh preferred embodiment shown in FIGS. 7A, 7C and 7D, wherein a prime symbol (') distinguishes like elements from the seventh preferred embodiment. In the modified version, the hinged element 646' includes a first or top portion 646a' and an opposing second or bottom portion 646b'. Each portion 646a', 646b' preferably includes a living hinge (not shown in FIG. 7B). Each portion 646a', 646b' may include a generally centrally located detent or depression 642' sized and shaped to receive at least a portion of the needle 616' therein when each portion 646a', 646b' is pivoted to the closed position (not shown in FIG. 7B). In the modified version, the closed portions 646a', 646b' "sandwich" or enclose at least a portion of the needle 616' on all sides at at least one point along the longitudinal axis A.

Referring to FIG. 7D, in the assembly 612 of the seventh preferred embodiment, a sealing element, as described in the previous embodiments, may not be necessary due to the size and/or shape of the adapter 620. In other words, the third seal 632 may be formed directly between the adapter 620 and the hub 611 of the barrel 614 or the syringe 610. Alternatively, the sealing element 618 and the adapter 620 may be integrally and unitarily formed as a single piece structure, such that the third seal 632 is formed between the sealing element 618 and the hub 611 of the barrel 614 or the syringe 610. Alternatively, the sealing element may be integrally and unitarily formed as a single piece structure with the needle shield 626.

Figure 7E:
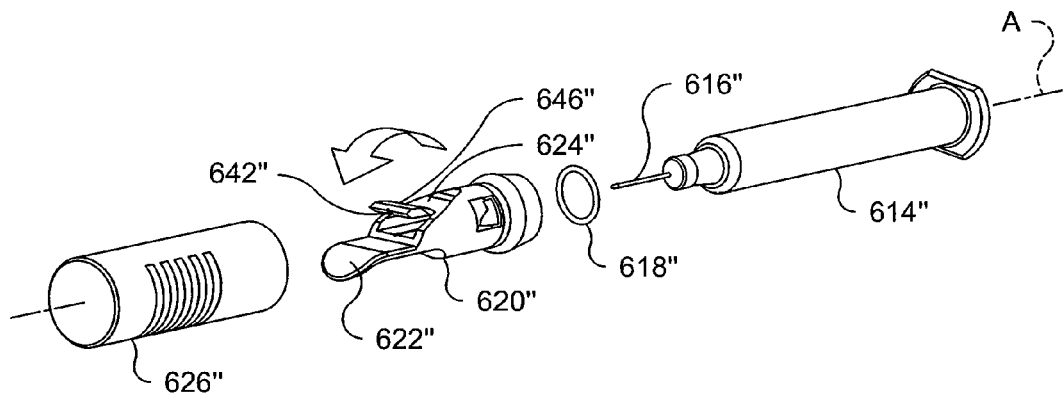
FIG. 7E is a perspective view of another modified version of a portion of the syringe and a portion of the assembly shown in FIG. 7A.

FIG. 7E shows another modified version of the seventh preferred embodiment shown in FIGS. 7A, 7C and 7D, wherein two prime symbols (") distinguish like elements from the seventh preferred embodiment. In the modified version, the hinged element 646" is preferably pivotable about an axis that extends generally, if not exactly, perpendicular to the longitudinal axis A. The hinged element 646" is preferably pivotable between an open position (FIG. 7E) and a closed position (not shown, but in the position when the hinged element 646" is moved in the direction of the arrow in FIG. 7E). The hinged element 646" preferably includes a living hinge, which attaches the hinged element 646" to the adapter 620", and a generally centrally located detent or depression 642" sized and shaped to receive at least a portion of the needle 616" therein when the hinged element 646" is pivoted to the closed position. In this modified version, the hinged element 646" "sandwiches" or encloses at least a portion of the needle 616" on all sides at at least one point along the longitudinal axis A in the closed position.

In the modified version of the seventh preferred embodiment shown in FIG. 7E, it is preferred that the needle shield 626" is pre-attached to and/or pre-assembled onto the adapter 620" prior to attaching and/or mounting either component to the needle 616" and/or barrel 614", such that the needle shield 626" surrounds generally the entire adapter 620", except for a proximal end portion of the adapter 620" that extends along the longitudinal axis A proximally further than a proximal or open end of the needle shield 626". In the above configuration, the hinged element 646" is preferably in at least a semi-open position or in the open position when the adapter 620" is inserted into and/or the needle shield 626" surrounds the adapter 620". It is preferred that the hinged element 646" is positioned in at least a semi-open position when the adapter 620" is pre-attached to the needle shield 626" to facilitate easier assembly onto the needle 616" and/or the barrel 614". It is preferred that immediately or shortly after the pre-attached needle shield 626" and adapter 620" is mounted and/or attached to the needle 616" and/or the barrel 614", a roller (not shown) or other mechanism would apply a force to the entire combination to close and/or snap the hinged element 646" by pushing on the section of needle shield 626" immediately adjacent to and outside of the semi-open hinged element 646".

Figure 8A:
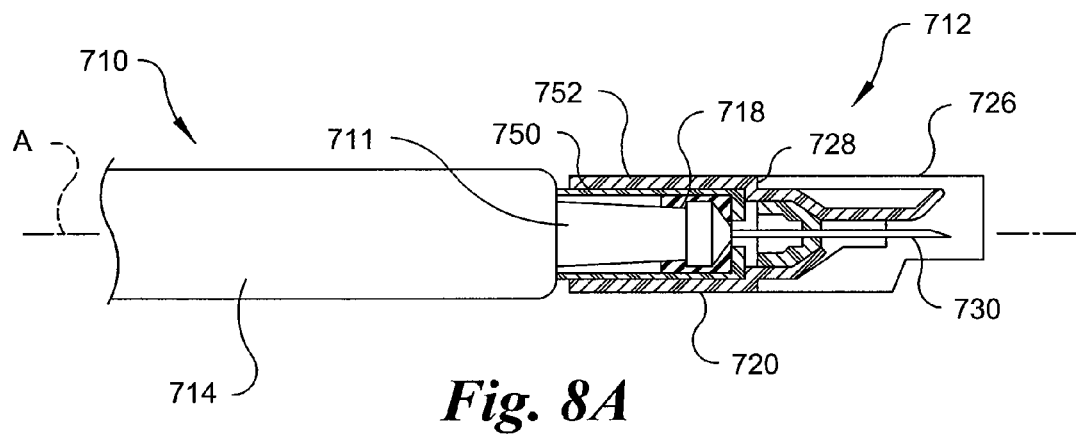
FIG. 8A is a partial cross-sectional elevation view of a portion of a syringe and an assembly according to an eighth preferred embodiment of the present invention shown in the first or combined configuration, wherein a sealing element and an adapter are shown in cross-section.
Figure 8B:
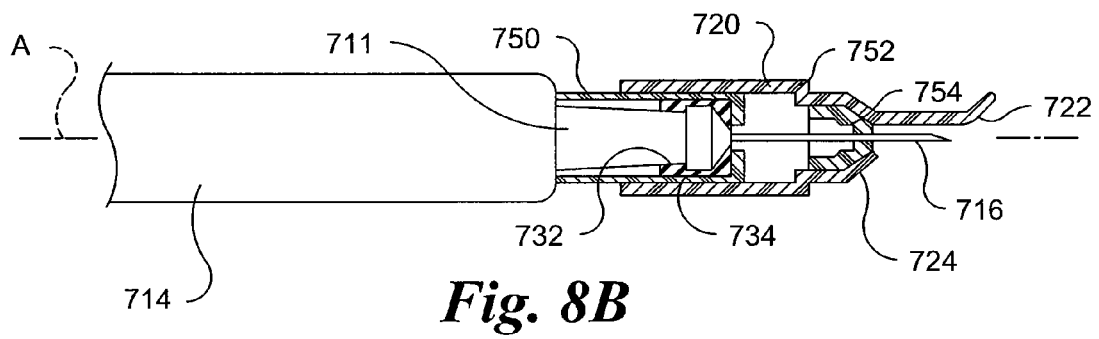
FIG. 8B is a partial cross-sectional elevation view of the syringe and a portion of the assembly shown in FIG. 8A, wherein the syringe and assembly are shown in a first or partially separated configuration.

Referring to FIGS. 8A-8B, an eighth preferred embodiment of the combination of the syringe 710 and the assembly 712 is shown. The reference numerals of the eighth preferred embodiment are distinguishable from those of the first preferred embodiment by a factor of seven hundred (700), but otherwise indicate the same elements as indicated in the first preferred embodiment, except as otherwise specified. The syringe 710 and the assembly 712 of the eighth preferred embodiment are substantially similar to those of the preferred embodiments described above. Specific similarities between the embodiments may be omitted herein for the sake of brevity and convenience, and therefore is not limiting.

The adapter 720 of the eighth preferred embodiment preferably includes a first component 750 generally fixedly connectable to at least a portion of the syringe 710, such as the hub 711 of the barrel 714. A second component 752 is preferably movably or slidably connected to the first component 752 and surrounds at least a portion thereof. FIG. 8A shows the two components 750, 752 in a retracted or storage position, and FIG. 8B shows the two components 750, 752 in an extended operative position. As shown in FIG. 8A, the terminal end 716a of the needle 716 extends distally along the longitudinal axis A beyond a distal end of the second component 752 in the retracted or storage position. As shown in FIG. 8B, the distal end of the second component 752 extends distally of the terminal end 716a of the needle 716 along the longitudinal axis A in the extended operative position. The first component 750 preferably compresses the sealing element 718 against the hub 711, which preferably creates the third and forth seals 732, 734. The second component 752 preferably includes a central guide 754 fixedly attached thereto, which preferably completely surrounds, supports and/or aligns at least a portion of the syringe 716 in both the retracted position (FIG. 8A) and the extended position (FIG. 8B).

In operation, the needle shield 726 may be removed from the second component 752 of the adapter 720 without moving the second component 752 from the retracted position (FIG. 8A) to the extended position (FIG. 8B). As described above, in this a configuration, at least the distal end 716a of the needle 716 extends beyond the distal end of the second component 752 along the longitudinal axis A, which allows for aspiration from a vial (not shown) for reconstitution of the medicament within the barrel 714. Following aspiration, the second component 752 may be moved distally or outwardly along the longitudinal axis A so as to be positioned directly above the distal end 716a of the needle 716. Moving the second component 752 further distally along the longitudinal axis A would shield and/or protect the needle 716, wherein the syringe 710 and assembly 712 are ready for injection. Alternatively, removal of the needle shield 726 may move the second component 752 into the extended position (FIG. 8B).

Figure 9:
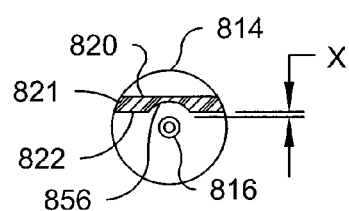
FIG. 9 is a front elevation view of a portion of a syringe and a portion of an assembly according to a ninth preferred embodiment of the present invention, the view is taken from a perspective similar to that of FIG. 4C.

FIG. 9 shows a cross-section of a portion of the distal protrusion 821 of a ninth preferred embodiment of the present invention. The reference numerals of the ninth preferred embodiment are distinguishable from those of the first preferred embodiment by a factor of eight hundred (800), but otherwise indicate the same elements as indicated in the first preferred embodiment, except as otherwise specified. The ninth preferred embodiment is substantially similar to the preferred embodiments described above. Specific similarities between the embodiments may be omitted herein for the sake of brevity and convenience, and therefore is not limiting.

As shown in FIG. 9, at least a portion of a bottom surface of the distal protrusion 821 or a portion of the first skin contacting surface 822 includes an indentation or raised portion 856 directly above or adjacent the needle 816. The indentation 856 is preferably located between two spaced-apart flat or planar portions, and is preferably concave in shape. The indentation 856 creates a increased vertical gap or spacing between a top surface of the needle 816 and the bottom surface of distal protrusion 821 or the first skin contacting surface 822, which is generally greater than the cannula gap distance X that would exist without the indentation 856. The distance between the indentation 856 and the outer periphery of the needle 816 is preferably three tenths of a millimeter (0.3 mm), but the distance is not limited to this exact dimension. This additional gap or increased clearance provided by the indentation 856 allows for proper sealing or enclosure of the distal end of the needle 816 by the needle shield (not shown in FIG. 9).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An assembly for use with a syringe having a barrel and a needle extending from a distal end thereof for delivering a medicament into a dermal layer of a patient's skin at an injection site, the assembly comprising:
 a sealing element surrounding and positioned over at least a portion of the distal end of the syringe, the sealing element having a cylindrically-shaped outer surface;
 a tubular-shaped adapter positioned over the distal end of the syringe, the adapter including:
  a cylindrically-shaped interior surface in contact with and surrounding the outer surface of the sealing element;
  a first surface of the adapter configured to contact a first area of the patient's skin, positioned at a distal end of the adapter and lying entirely in a first plane generally parallel to a longitudinal axis of the needle; and
  a second, surface of the adapter configured to contact a second area of the patient's skin, the second surface being different than the first surface, spaced from the needle and lying entirely in a second plane at a predetermined angle relative to the first plane; and
 a needle shield at least partially surrounding and removably positioned over at least of the adapter, the sealing element, and the syringe barrel,
 wherein the adapter is fixedly and permanently attached to the distal end of the barrel of the syringe and longitudinal movement of the needle is fixed relative to the first surface of the adapter during orientation of the needle relative to the injection site, insertion of the needle in the patient's skin at the injection site and injection of the medicament,
 wherein longitudinal movement of the sealing element is fixed relative to the adapter, and
 wherein the first surface of the adapter and the second surface of the adapter contact with the first area and second area, respectively, of the patient's skin at the injection site during delivery of the medicament into the dermal layer.

2. The assembly of claim 1, further comprising:
 a first seal formed between the needle shield and one of the adapter, the sealing element, and the syringe barrel;
 a second seal formed between the needle shield and the terminal end of the needle; and
 at least a third seal formed between the sealing element and one of the syringe and the adapter.

3. The assembly of claim 2, wherein the adapter, the sealing element, and the needle shield are provided in an assembled state as a sub-assembly for assembly with the syringe.

4. A combination of a syringe and an assembly for delivering a medicament into a dermal layer of a patient's skin at an injection site, the combination comprising:
 the syringe including a barrel and a needle extending from a distal end thereof;
 the assembly including:
 a tubular-shaped adapter positioned over at least a portion of the distal end of the syringe, the adapter including:
  a first su face of the adaptor configured to contact a first area of the patient's skin, positioned at a distal end of the adapter and lying entirely in a first plane generally parallel to a longitudinal axis of the needle; and
  a second surface of the adaptor configured to contact a second area of the patient's skin, the second surface being different than the first surface, positioned proximally relative to the terminal end of the needle and lying entirely in a second plane at a predetermined angle relative to the first plane;
 a needle shield at least partially surrounding and removably positioned over a least one of the adapter and the syringe barrel; and
 a sealing element surrounding and positioned over at least a portion of the distal end of the syringe, the sealing element having a cylindrically-shaped outer surface, a cylindrically-shaped interior surface of the adapter in contact with and surrounding the outer surface of the sealing element,
 wherein the adapter is fixedly and permanently attached to the distal end of the barrel of the syringe and longitudinal movement of the needle is fixed relative to the first surface of the adaptor during orientation of the needle relative to the injection site, insertion of the needle in the patient's skin at the injection site and injection of the medicament,
 wherein longitudinal movement of the sealing element is fixed relative to the adapter, and
 wherein the first surface of the adaptor and the second surface of the adaptor are in contact with the first area and second area, respectively, of the patient's skin at the injection site du ing delivery of the medicament into the derma layer.

5. The combination of claim 4, further comprising:
 a first seal formed between the needle shield and one of the adapter, the sealing element and the syringe barrel;
 a second seal formed between the needle shield and the terminal end of the needle; and
 at least a third seal formed between the sealing element and the syringe.

* * * * *